United States Patent [19]

Logothetis et al.

[11] Patent Number: 4,536,241

[45] Date of Patent: Aug. 20, 1985

[54] METHOD OF MAKING A TITANIUM DIOXIDE OXYGEN SENSOR ELEMENT WITH FAST TRANSIENT RESPONSE

[75] Inventors: Eleftherios M. Logothetis, Birmingham; William J. Kaiser, Farmington Hills, both of Mich.

[73] Assignee: Ford Motor Company, Dearborn, Mich.

[21] Appl. No.: 604,662

[22] Filed: Apr. 27, 1984

[51] Int. Cl.³ .................... B05D 5/12; G01N 27/12
[52] U.S. Cl. ............................. 156/89; 204/424; 338/34; 427/126.2; 427/126.3
[58] Field of Search ............. 156/89; 204/424, 431; 338/34; 427/126.2, 126.3

[56] References Cited

U.S. PATENT DOCUMENTS

| | | | |
|---|---|---|---|
| 3,893,230 | 7/1975 | Stadler et al. | 156/89 |
| 3,932,246 | 1/1976 | Stadler et al. | 156/89 |
| 4,151,503 | 4/1979 | Cermak et al. | 204/424 |
| 4,187,486 | 2/1980 | Takahashi et al. | 338/34 |
| 4,335,369 | 6/1982 | Taniguchi et al. | 338/34 |
| 4,417,228 | 11/1983 | Takami et al. | 338/34 |
| 4,485,369 | 11/1984 | Ushida | 338/34 |
| 4,504,522 | 3/1985 | Kaiser et al. | 427/126.3 |

Primary Examiner—Caleb Weston
Attorney, Agent, or Firm—William E. Johnson; Clifford L. Sadler

[57] ABSTRACT

This specification discloses a method of making a titanium dioxide element (20) which can be used as an oxygen sensing element. The method involves the selection of at least a pair of electrically conductive leads (12—12) which resist oxidation at high temperatures. The leads are placed in a position generally close to one another with a slurry bridgeable space therebetween. Slurry (14) is applied to the pair of spaced leads. The slurry contains titanium dioxide, an organic heat decomposable binder, and an organic solvent. The slurry is one that when applied to the pair of spaced leads the surface tension of the slurry draws it into a compact generally spherical shape about the pair of spaced leads. The slurry is dried, heated and sintered so that the titanium dioxide particles contained in the slurry are sintering together to form a titanium dioxide oxygen sensing element bridging the bridgeable space between the pair of spaced leads. The titanium dioxide sensing element has a thickness in a range of 20–200 micrometers and a density in a range of 60–80% of the theoretical value of density of titanium dioxide which is 4.26 grams per cubic centimeter. The titanium dioxide oxygen sensing element so formed is characterized as a fast responding element in sensing ambient changes from oxygen-rich to oxygen-lean conditions and vice-versa.

5 Claims, 6 Drawing Figures

U.S. Patent  Aug. 20, 1985  Sheet 1 of 2  4,536,241
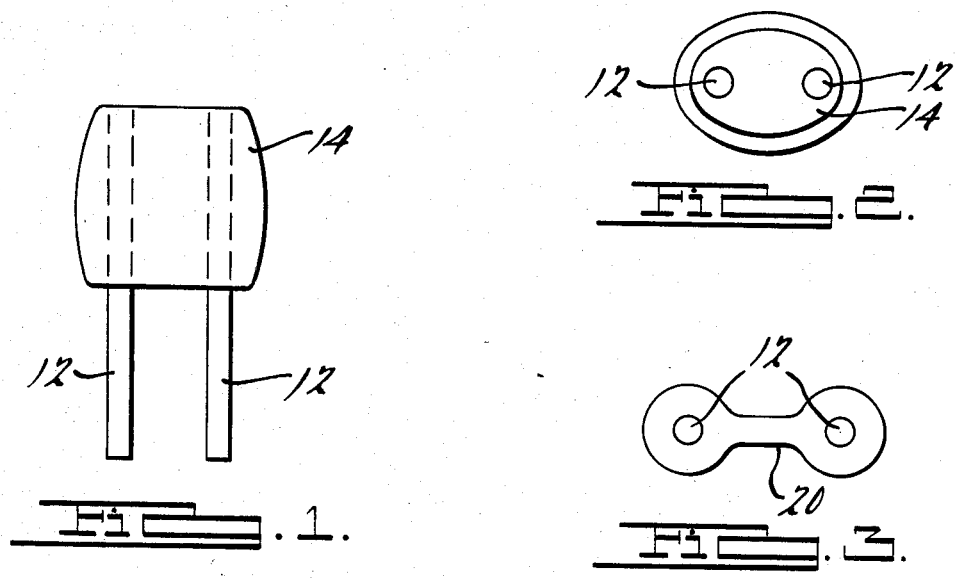
FIG. 1.
FIG. 2.
FIG. 3.
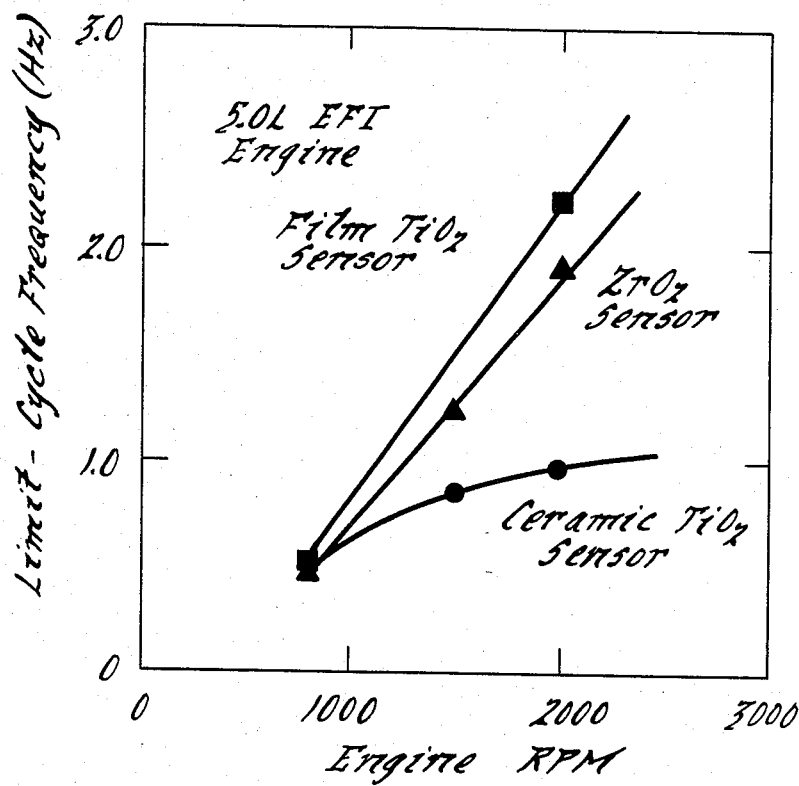
FIG. 4.

METHOD OF MAKING A TITANIUM DIOXIDE OXYGEN SENSOR ELEMENT WITH FAST TRANSIENT RESPONSE

TECHNICAL FIELD

This specification is directed to a method of making a titanium dioxide oxygen sensor element. In general, the sensor element so made is characterized as being a "microchip" titanium dioxide sensor element.

BACKGROUND AND PRIOR ART STATEMENT

For a number of years, oxygen sensors have been employed in motor vehicles in conjunction with the use of three-way catalyst systems for the treatment of exhaust gases from internal combustion engines. Generally, the oxygen sensor and three-way catalyst are coupled with a feedback control system of an air/fuel ratio metering device to control the stoichiometric air/fuel ratio being fed to the internal combustion engine at any particular time. If the oxygen sensor detects too much oxygen in the exhaust gases after passage of those gases through the three-way catalyst, more fuel is supplied to the engine. On the other hand, if the oxygen sensor detects an insufficient amount of oxygen in the exhaust gases, then the feedback control system decreases the amount of fuel being fed to the internal combustion engine.

One type of oxygen sensor which has been developed for such an application uses zirconium oxide, zirconia, as the sensing element. This material has been used in oxygen sensors for millions of automobiles now on the road in the United States.

A titanium dioxide, titania, type of oxygen sensor based on ceramic processing technology has been developed by Ford Motor Company. The particular ceramic titanium dioxide sensor developed by Ford Motor Company is covered by a number of U.S. patents, for example: U.S. Pat. Nos. 3,893,230; 3,911,386; 3,932,246; 3,933,028; 3,959,765; 4,001,758; and 4,151,503.

These patents are representative of the patents Ford Motor Company has obtained in the field of titanium dioxide oxygen sensors. However, these ceramic type titanium dioxide sensors have a slower response time than the zirconia sensor developed by others. By slower response time we mean that it takes a longer period of time for the titania sensor, made by ceramic processing technology, to detect a switch from oxygen-rich to oxygen-lean conditions, or vice-versa, than does the zirconia sensor.

This slower response to the ceramic type titania sensor does not have any effect on the feedback control system, and thus engine operation, as long as the response of the feedback air/fuel (A/F) control system is limited by a slow fuel metering device such as a feedback carburetor. The inherent mechanical limitations of the carburetor make this device much slower responding than the ceramic type titania sensor so the system itself does not in any manner note the slower response time of the titania sensor when this sensor replaces a zirconia sensor. However, when the feedback control system uses a fast reponse fuel metering device, such as an electronic fuel injection system, then the feedback system could be hampered by the slower response time of the ceramic type titania sensor.

The present development was brought about in order to obtain a titania sensor with a faster response time than the ceramic type titania sensor. It was a principal purpose of our investigation to develop titanium dioxide elements for sensors which have response times sufficiently fast that the fuel injected type of feedback system would not notice a delay in receiving a control signal because of a delay in the oxygen sensor's ability to detect changes from oxygen-rich to oxygen-lean conditions and vice-versa. We accomplished this purpose by developing titanium dioxide elements for sensors of the so-called "microchip" variety which will hereafter be described in greater detail.

The ceramic type titanium dioxide ($TiO_2$) materials developed by Ford for oxygen sensing applications have a density in the range from 60–80% of the theoretical value. The microstructure of this type of material consists of interconnected $TiO_2$ particles with a size of a few micrometers separated by interconnected pores with a similar size. The addition of catalytic metals (Pt, Rh) into the porous $TiO_2$ ceramic accelerates the oxygen transfer process between the solid and the ambient gas and leads to a substantial improvement in the ceramic type sensor response time.

Our studies have indicated that the response time of such noble metal impregnated ceramic $TiO_2$ sensors is limited to a large degree by the gas transport process through the pores of the ceramic sensor material. One approach for decreasing the effect of this gas transport process is to decrease the thickness of the $TiO_2$ material; for example, by replacing the ceramic type sensor material with a film. If the film is made dense, its thickness must be kept small, less than 10 um (um means micrometers), otherwise oxygen diffusion in the bulk of the solid would result in unacceptably long response times. On the other hand, films with a small thickness, less than 10 um, may not have the required durability since, for example, some erosion of the film could occur because of the passage of the exhaust gases of an engine thereover. It is thus desirable to prepare films thicker than 10 um, preferably thicker than 20–30 um. However, the response time of sensors using such thick films would be unacceptably long (due to bulk diffusion of oxygen) unless the film has an optimized porosity and microstructure that minimizes the contribution of bulk diffusion and gas transport through the pores to the sensor response delay.

The preparation of films of metal oxides, and $TiO_2$ in particular, has been discussed extensively in the literature. Reported preparation methods include thick film techniques using sputtering, thermal evaporation, and chemical vapor deposition. However, most of the prior art $TiO_2$ film preparation methods are not suitable for oxygen sensor applications because they do not provide the film composition, microstructure, and electrical and mechanical properties required for fast responding oxygen sensors. For example, sputtering deposition tends to give dense films which would not provide fast oxygen sensors unless their thickness is kept undesirably small. Amorphous films with densities much smaller than theoretical (in the range of 50–80%) have been prepared by various techniques. However, these films are unstable at the high temperatures of the automotive exhaust and do not generally have the required electrical properties. High temperature annealing to convert them to the stable rutile structure has the tendency to change them to dense materials.

A common and commercially used technique for thick film preparation is screen printing from inks. U.S.

Pat. No. 4,335,369 to Taniguchi et al describes a method of preparing thick $TiO_2$ films by screen printing from $TiO_2$ pastes for oxygen sensing applications. Sensors using these films were found to be faster than those employing ceramic $TiO_2$ materials. The method described in the above patent, however, is tedious and time consuming because it was found that the optimum film thickness of 50-100 um with the required microstructure could not be obtained unless the $TiO_2$ paste was deposited in approximately 15 um steps, each step followed by a long drying period (more than one hour).

Another commercially important film preparation technique is the technique of chemical vapor deposition (CVD). Metal oxides including $TiO_2$ have been prepared by CVD from several inorganic and organic compounds. Of the organic compounds, tetraisopropyl titanate $Ti(C_3H_7O)_4$ has been used for the preparation of dense, hard and abrasion-resistant titanium oxide (with unspecified Ti/O ratio) protective coatings of glassware. These materials, however, are amorphous, unstable at elevated temperatures, and do not have the electrical properties required for oxygen sensor applications.

S. Sakurai and M. Watenabe (Rev. Elect. Comm. Lab. 11, 178, 1963) decomposed $Ti(C_3H_7O)_4$ [and $Ti(C_2H_5O)_4$] in vacuum above 900° C. to obtain $TiO_2$ films with the rutile structure. These films, however, were found to be very dense (99% of the theoretical density). This method of $TiO_2$ film preparation is not therefore suitable for obtaining fast $TiO_2$ elements for use in oxygen sensors.

More recently, Yokozawa et al (Japan J. Appl. Phys. 7, 96, 1968) investigated the preparation of thin titanium oxide films on silicon wafers from $Ti(C_3H_7O)_4$ for possible use in photo-etching technology. They found that thermal decomposition of $Ti(C_3H_7O)_4$ in an atmosphere of nitrogen and oxygen in the range of 320°-540° C. gave films consisting of very fine crystallites of anatase phase. These films are apparently unstable since the anatase phase films were found to possess the remarkable property of being easily etched (4-60 A°/sec.) by a diluted HF solution. In contrast, normal $TiO_2$ cannot be etched with any known etching agent (except KOH above 150° C.).

It is thus desirable to develop titania thick film preparation techniques that provide the microstructure and electrical properties required for fast responding elements for use in oxygen sensors. The techniques so developed must also be acceptable for high volume production of elements for oxygen sensors.

In copending U.S. patent application Ser. No. 589,790, filed Mar. 15, 1984, we have described a $TiO_2$ oxygen sensor and preparation method based on films grown by chemical vapor deposition (CVD). As discussed in that application, these films do not have the problems of the CVD titania materials of the prior art and have provided elements for making fast responding oxygen sensors. In the present specification we describe another method for preparing titania films which also avoids the problems of the prior art ceramic type sensors.

DISCLOSURE OF THE INVENTION

The invention is directed to a method of making a titanium dioxide element and, more particularly, to a method of making a titanium dioxide element which can be used as an oxygen sensing element.

In accordance with the general teachings of the method of our invention, the method has the following steps. At least a pair of electrically conductive leads are selected. The leads are formed of a material which is resistant to thermal degradation at temperatures normally found in exhaust gases from operation of an internal combustion engine. The pair of leads are placed in a position generally close to one another with a slurry bridgeable space therebetween.

A titanium dioxide containing slurry is applied to the pair of spaced leads. The titanium dioxide containing slurry has the following characteristics. The slurry is formed on a volume basis as follows: 10-50% titanium dioxide, 5-15% of an organic heat decomposable binder, and 85-35% of an organic solvent. The titanium dioxide in the slurry consists of particles of substantially rutile phase titanium dioxide having a size range from 0.5-10 micrometers and a surface area of 0.1-3 square meters per gram ($m^2$/g). By forming the slurry in this manner, when a measured amount of the slurry is applied to the pair of spaced leads, the surface tension of the slurry draws the slurry into a compact, generally cylindrical shape about the pair of spaced leads.

The slurry applied to the pair of spaced leads is dried. The remaining of the slurry attached to the pair of spaced leads is then heated and sintered so that the titanium dioxide particles contained in the slurry sinter together to form a titanium dioxide oxygen sensing element bridging the bridgeable space between the pair of spaced leads. The titanium dioxide sensing element so formed has a thickness in a range of 20-200 micrometers and a density in a range of 60-80% of the theoretical value of density of titanium dioxide which is 4.26 grams per cubic centimeter.

In this manner a titanium dioxide oxygen sensing element is formed between the pair of spaced leads, which is characterized as a fast responding element in sensing ambient changes from oxygen-rich to oxygen-lean conditions and vice-versa. Such an oxygen sensing element may be formed into a device for sensing oxygen for use in conjunction with an internal combustion engine powering a motor vehicle.

In accordance with more detailed teachings of the method of this invention, the drying of the titanium dioxide slurry may take place at a temperature of not more than 200° C. for a period of time not exceeding 4 to 5 hours.

The heating and sintering operation may take place at a final temperature in a range of 1100°-1250° C. for a period of time of 1-2 hours.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in connection with the accompanying drawings, wherein like reference characters indicate like parts throughout the several figures, and in which:

FIG. 1 is a schematic view in elevation of a titanium dioxide element in an early manufacturing step as manufactured in accordance with the method of this invention;

FIG. 2 is a plan view of the titanium dioxide element of FIG. 1 as that element would be in an early stage of its manufacture;

FIG. 3 is a schematic drawing in plan view of the titanium dioxide element of FIGS. 1 and 2 in a later stage of its manufacture;

FIG. 6 is a graphical presentation of the dependence of the frequency of the feedback control of the air to fuel ratio of an internal combustion engine on engine rpm for a film $TiO_2$ sensor according to this invention, a $ZrO_2$ sensor, and a ceramic $TiO_2$ sensor.

BEST MODE AND INDUSTRIAL APPLICABILITY

Figure 4:
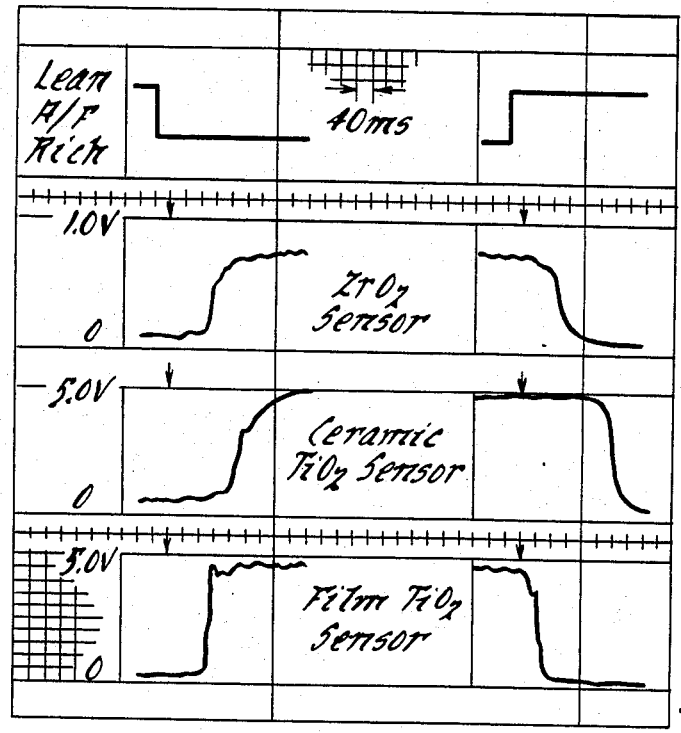
FIGS. 4 and 5 are comparisons of the transient reponse of typical $ZrO_2$ sensor, a ceramic $TiO_2$ sensor, and a film $TiO_2$ sensor made in accordance with the teaching of this invention, each comparison being obtained upon a different step of comparison conditions.

The following description is what we consider to be a preferred embodiment of the method of our invention of making a titanium dioxide element which can be used as an oxygen sensing element. The following description also sets forth what we now contemplate to be the best mode of carrying out the method of our invention. The description is not intended to be a limitation upon the broader principles of the method and while preferred materials are used to illustrate the preferred embodiment it does not mean that other materials cannot be used in the method of this invention.

Preferred Embodiment

A preferred embodiment of making a titanium dioxide element is set forth below. In this preferred embodiment the titanium dioxide element so made is designed for use as an oxygen sensing element. The element has particular utility in sensing the concentration of oxygen in an exhaust gas stream being released from an internal combustion engine or in the sensing of oxygen in any exhaust gas stream issued from a process in which a carbon containing fuel is being burned.

In accordance with this preferred embodiment, and as best seen in FIGS. 1-3, at least a pair of electrically conductive leads 12—12 are selected. In accordance with the preferred teaching, the leads 12—12 are arranged so that they are generally parallel to one another and separated by a distance in the order of about a thickness of one of the leads. In the preferred embodiment the leads are formed from a suitable wire. For example, electrode wire having a fine diameter may be used to form the leads. Fine diameter wire, for example, may have a diameter in a range of 0.001-0.020 inch. The leads may also be formed of relatively thin conductive foil material or any suitable material which may conduct electricity. The material should be resistant to thermal degradation at temperatures normally found in exhaust gases generated from the operation of an internal combustion engine or from a fuel burning process. For example, the wires may be made from material such as platinum, platinum alloys, refractory materials which are conductive, refractory materials which are cladded with corrosion resistant layers as well as any other material known to the skilled artisan which can work as an electrode material and also can withstand the temperatures to which oxygen sensors are subjected.

As shown in FIGS. 1-2, the pair of leads are positioned generally close to one another with a space therebetween. As shown in the drawings, the pair of leads are generally parallel to one another. The space between the pair of leads is generally a space which is bridgeable by a titanium dioxide containing slurry which will be described hereinbelow. By a bridgeable space we mean one that when the titanium dioxide slurry is placed on the wires, the surface tension of the slurry will hold it in position about the pair of spaced wires and the slurry will not fall or otherwise drop therefrom. While in the preferred embodiment the pair of leads are generally parallel to one another, this condition need not be true. The only real requirement is that there be at least a pair of leads and that they be separated from one another by a slurry bridgeable space therebetween.

A titanium dioxide containing slurry 14 is applied to the pair of spaced leads 12—12. The slurry is applied by any suitable applying method, for example, by being placed upon the pair of spaced leads by means of a suitable syringe or other volume dispensing device. The titanium dioxide containing slurry bridges the slurry bridgeable space between the pair of leads as is shown best in FIGS. 1-2. The slurry is formed on a volume basis of 10-50% titanium dioxide, 5-15% of an organic heat decomposable binder, and 85-35% of an organic solvent, all of which elements will be described in greater detail hereinbelow. Because of the surface tension of the slurry, the slurry is drawn into a compact, generally cylindrical shape about the pair of spaced leads.

The titanium dioxide powder used to form the titanium dioxide containing slurry 14 is made up of particles of substantially pure rutile phase. The rutile phase powder consists of particles having a size in a range of 0.5-10 micrometers with a surface area in a range of 0.1-3 square meters per gram ($m^2/g$). It is important that substantially only rutile phase titanium dioxide powder be used as titanium dioxide films containing other than this phase material are prone to cracking during cooling from high temperatures in the range of 1100°-1200° C., which temperatures are encountered in sintering.

As stated above, the titanium dioxide containing slurry contains 5-15% of an organic heat decomposable binder. The binder is one of the major factors in determining the surface tension of the titanium dioxide containing slurry. The binder may be a standard ceramic processing binder. One material which we have found acceptable is a trade material called Butvar B-76 sold by Monsanto. This binder is polyvinyl butryl. When the preferred Butvar B-76 binder is used, it should form 5-15% by volume of the titanium dioxide containing slurry and the titanium dioxide should be 10-50% by volume. When the preferred Butvar B-76 binder is used, the ratio of the weight of rutile material to the weight of the binder in the slurry should be in the range of 9-12.

The third component making up the titanium dioxide containing slurry is a suitable organic solvent. A number of different organic solvents may be used, for example: acetone, toluene and alcohols. The amount of solvent used to make the titanium dioxide containing slurry depends not only on the method of deposition of the slurry but also the thickness or diameter of the electrically conductive leads 12—12 and the final film thickness desired for the oxygen sensing element to be made by the method of this invention as well as the element's porosity.

The three constituents of the titanium dioxide containing slurry 14 are mixed together in proportions so that the following characteristics are obtained when the slurry is applied to the pair of electrically conductive leads 12—12. The surface tension of the slurry should be such that the slurry is drawn into a compact generally cylindrical shape as best seen in FIGS. 1-2 about the pair of electrically conductive leads. When the slurry is first applied it will have have a cross-section shape, generally egg-shaped (as shown in FIG. 2), but it will be in a position which bridges the slurry bridgeable space between the electrically conductive leads.

After application, the titanium dioxide containing slurry 14 is allowed to dry in air at room temperature or at a temperature somewhat elevated from room temperature, but generally less than 200° C., for a period of time generally not required to exceed 4-5 hours at a low temperature and 2-3 hours at an elevated temperature. This drying permits some of the organic solvent to be evaporated along with any low boiling point material which may be part of the organic heat decomposable binder which is also a constituent of the titanium dioxide containing slurry.

After the drying operation, the remaining of the titanium dioxide containing slurry which is on the electrically conductive leads 12—12 is heated and sintered. The purpose of this operation is to sinter together the titanium dioxide particles contained in the slurry to form a titania dioxide oxygen sensing element 20, best seen in FIG. 3. The heating and sintering operation is generally carried out at a final temperature in a range of 1100°-1250° C. for a period of 1-2 hours. The material may be heated to this final temperature from room temperature at a rate of about 30° C. per minute. During the heating and sintering operation, any remaining organic solvent in the slurry is driven off and the organic heat decomposable binder is broken down and driven off, whereby the sintering of the titanium dioxide particles can take place.

The completed titanium dioxide sensing element 20, as shown in FIG. 3, has a thickness in the slurry bridgeable space between the electrically conductive leads 12—12 in the range of 20-200 micrometers. The titanium dioxide material also has a density in a range of 60-80% of the theoretical value of density of titanium dioxide which is 4.26 grams per cubic centimeter. This titanium dioxide sensing element is characterized as being a "microchip" titanium dioxide sensor element having a fast response time in sensing ambient changes from oxygen-rich to oxygen-lean conditions and vice-versa. If desired, the element may be impregnated with a noble metal catalyst such as described in previously granted, Ford Motor Company assigned, U.S. Pat. No. 4,225,559, to improve the low temperature characteristics of any oxygen sensor made from this element.

Figure 5:
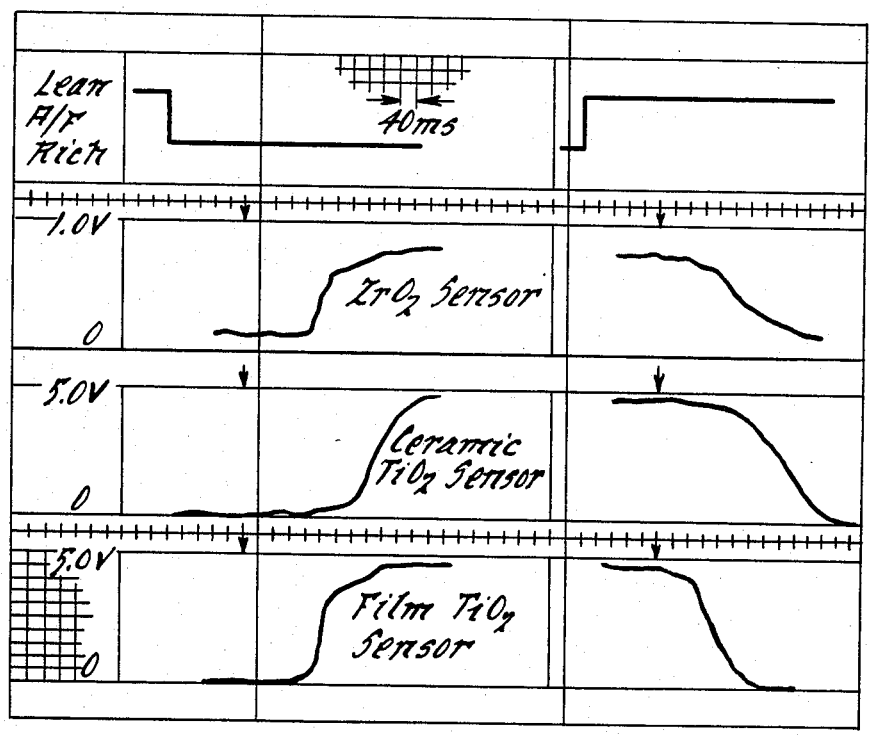

FIG. 4 of the drawings compares the transient response of film $TiO_2$ sensors made with sensing elements made in accordance with the teachings of this invention with the transient response of the ceramic $TiO_2$ sensor and $ZrO_2$ sensors of the prior art. In the comparison set forth in FIG. 5, a 5.0 liter internal combustion engine was operated at a constant rpm/load condition and the air/fuel ratio was cycled from lean to rich. In the comparison set forth in FIG. 4, the engine rpm was 2000 and the temperature of the sensor was about 700° C. In the case of the titanium dioxide sensors, a 5.0 volt power supply was applied across a sensor combined with a resistor and the sensor output voltage was measured across the resistor. The same type of graph is set forth in FIG. 5. In FIG. 5, however, the engine was operated at 800 rpm and the temperature of the sensors was approximately 350° C.

It can be clearly seen from FIGS. 4 and 5 that the film $TiO_2$ sensor made from the sensor element manufactured in accordance with the method of our invention is not only substantially faster than the prior art ceramic $TiO_2$ sensor, but also faster than the prior art $ZrO_2$ sensor.

FIG. 6 compares the frequency of the limit cycle feedback operation of the 5.0 liter engine when each of the three different sensors was used. The film $TiO_2$ sensor made from a sensing element made in accordance with the teachings of the method of this invention gives the highest frequency as expected from the fact it has the shortest response time. A higher frequency generally results in a smaller amplitude modulation of the air/fuel ratio around stoichiometry and should lead to an improved system performance. This demonstrates that a $TiO_2$ sensor made from a $TiO_2$ sensor element made in accordance with the teachings of the present invention is not only substantially faster than the prior art ceramic $TiO_2$ sensor, but also faster than the $ZrO_2$ sensor.

In summary, this invention describes a simple and inexpensive method and defines the necessary conditions to make a "microchip" type of $TiO_2$ oxygen sensing element which may be used in a $TiO_2$ oxygen sensing sensor. The element so made has the necessary electrical properties as well as a microstructure that results in a very fast transient response to changes in the oxygen pressure of the exhaust gases.

While particular embodiments of the invention have been illustrated and described, it will be obvious to those skilled in the art that various changes and modifications may be made to the method of our invention without departing from the invention and it is intended to cover in the appended claims all such modifications and equivalents as fall within the true spirit and scope of this invention.

We claim:

1. A method of making a titanium dioxide element which can be used as an oxygen sensing element, which method comprises the steps of:

selecting at least a pair of electrically conductive leads, said leads being formed of a material which is resistant to thermal degradation at temperatures normally found in exhaust gases from operation of an internal combustion engine;

placing said pair of leads in a position generally close to one another with a slurry bridgeable space therebetween;

applying to said pair of spaced leads a titanium dioxide containing slurry having the following characteristics: said slurry being formed on a volume basis of 10-50% titanium dioxide, 5-15% of an organic heat decomposable binder, and 85-35% of an organic solvent, and said titanium dioxide in said slurry consisting of particles of substantially rutile phase titanium dioxide having a size range from 0.5-10 micrometers and a surface area of 0.1-3 square meters per gram ($m^2/g$), whereby when a measured amount of said slurry is applied to the pair of spaced leads, the surface tension of said slurry draws said slurry into a compact, generally cylindrical shape about the pair of spaced leads;

drying said slurry applied to said pair of spaced leads so that said leads and remaining of said slurry attached thereto may be subjected to a heating and sintering operation;

heating and sintering said pair of spaced leads and remaining of said slurry attached thereto so that said titanium dioxide particles contained in said slurry sinter together to form a titanium dioxide oxygen sensing element bridging said bridgeable space between said pair of spaced leads, said titanium dioxide sensing elements having a thickness in a range of 20-200 micrometers and a density in a range of 60-80% of the theoretical value of density of titanium dioxide which is 4.26 grams per cubic centimeter, whereby said titanium dioxide oxygen sensing element is characterized as a fast responding element in sensing ambient changes from oxygen-rich to oxygen-lean conditions and vice-versa.

2. The method of claim 1, wherein said drying operation is carried out at a temperature not to exceed 200° C. for a time period generally not exceeding 4-5 hours.

3. The method of claim 1, wherein said heating and sintering operation is carried out at a temperature in a range of 1100°-1250° C. for a period of 1-2 hours.

4. The method of claim 2, wherein said heating and sintering operation is carried out at a temperature in a range of 1100°-1250° C. for a period of 1-2 hours.

5. The method of claim 1, wherein said titanium dioxide sensing element has a thickness of about 20 to 120 micrometers.

* * * * *